United States Patent

Hunt et al.

(10) Patent No.: US 10,028,721 B2
(45) Date of Patent: Jul. 24, 2018

(54) BIPHASIC DEFIBRILLATOR WAVEFORM WITH ADJUSTABLE SECOND PHASE TILT

(75) Inventors: David K. Hunt, Nashua, NH (US); James K. Russell, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 790 days.

(21) Appl. No.: 13/377,905

(22) PCT Filed: Jun. 2, 2010

(86) PCT No.: PCT/IB2010/052468
§ 371 (c)(1),
(2), (4) Date: Feb. 2, 2012

(87) PCT Pub. No.: WO2010/146492
PCT Pub. Date: Dec. 23, 2010

(65) Prior Publication Data
US 2012/0123492 A1  May 17, 2012

Related U.S. Application Data

(60) Provisional application No. 61/218,547, filed on Jun. 19, 2009.

(51) Int. Cl.
A61N 1/00 (2006.01)
A61B 8/00 (2006.01)
A61B 8/08 (2006.01)
A61B 5/00 (2006.01)

(52) U.S. Cl.
CPC .............. *A61B 8/00* (2013.01); *A61B 5/0048* (2013.01); *A61B 5/0051* (2013.01); *A61B 8/085* (2013.01); *A61B 8/485* (2013.01); *A61B 8/5223* (2013.01)

(58) Field of Classification Search
USPC ....................................................... 607/4–5
See application file for complete search history.

(56) References Cited

U.S. PATENT DOCUMENTS

| 4,800,883 A | 1/1989 | Winstrom |
| 4,821,723 A | 4/1989 | Baker, Jr. et al. |
| 4,850,357 A | 7/1989 | Bach, Jr. |
| 4,953,551 A | 9/1990 | Mehra et al. |
| 5,083,562 A | 1/1992 | de Coriolis et al. |
| 5,230,336 A | 7/1993 | Fain et al. |

(Continued)

FOREIGN PATENT DOCUMENTS

| EP | 1530983 A2 | 5/2005 |
| JP | H1057508 A | 3/1998 |

(Continued)

OTHER PUBLICATIONS

Kerber et al: "Energy, Current, and Success in Defibrillation and Cardioversion: Clinical Studies Using an Automated Impedance-Based Method of Energy Adjustment"; Circulation, 988; 77, pp. 1038-1046.

*Primary Examiner* — Alyssa M Alter

(57) ABSTRACT

A defibrillator produces a biphasic defibrillation pulse waveform with adjustable tilt for the second phase. The tilt of the second phase of the biphasic waveform can be controllably adjusted by selectively switching a current path which bypasses the patient during delivery of the second phase of the pulse. The inventive biphasic waveform can be delivered by a defibrillator with a single capacitance.

13 Claims, 4 Drawing Sheets

(56) References Cited

U.S. PATENT DOCUMENTS

| | | | |
|---|---|---|---|
| 5,352,239 A | 10/1994 | Pless | |
| 5,725,560 A * | 3/1998 | Brink | .................................. 607/5 |
| 5,735,879 A | 4/1998 | Gliner et al. | |
| 5,749,904 A | 5/1998 | Gliner et al. | |
| 5,803,927 A | 9/1998 | Cameron et al. | |
| 5,991,658 A | 11/1999 | Brewer et al. | |
| 6,539,255 B1 | 3/2003 | Brewer et al. | |
| 6,714,818 B1 | 3/2004 | Fishler et al. | |

FOREIGN PATENT DOCUMENTS

| | | |
|---|---|---|
| JP | 2001506157 A | 5/2001 |
| WO | 98296841 A1 | 6/1998 |

* cited by examiner

BIPHASIC DEFIBRILLATOR WAVEFORM WITH ADJUSTABLE SECOND PHASE TILT

This application claims the benefit of international application number PCT/IB2010/052468, filed Jun. 2, 2010, which claims the benefit of U.S. provisional application Ser. No. 61/218,547, filed Jun. 19, 2009.

This invention relates to defibrillators for resuscitating patients stricken with cardiac arrest and, in particular to defibrillators which produce biphasic shock waveforms.

Sudden cardiac death is a leading cause of death in the United States. A common cause of sudden cardiac death is ventricular fibrillation, in which the heart's muscle fibers contract without coordination. This lack of coordinated myocardial activity results in a loss of the ability of the heart to effectively pump blood, thereby interrupting normal blood flow to the body. The only effective treatment for ventricular fibrillation is electrical defibrillation, which applies an electrical shock to the patient's heart. The strong defibrillation shock stops all electrical activity by the heart. Thereafter, the body's autonomous nervous system automatically resumes the application of coordinated electrical pulsation of the heart.

To be effective, the defibrillation shock must be delivered to the patient within minutes of the onset of ventricular fibrillation. Studies have shown that defibrillation shocks delivered within one minute after ventricular fibrillation begins achieve up to a 100% survival rate. The survival rate falls to approximately 30% if 6 minutes elapse before the shock is administered. Beyond 12 minutes, the survival rate approaches zero.

One way of delivering rapid defibrillation shocks is through the use of implantable defibrillators. Implantable defibrillators are surgically implanted in patients who have a high likelihood of needing electrotherapy in the future. Implanted defibrillators typically monitor the patient's heart activity and automatically supply electrotherapeutic pulses directly to the patient's heart when indicated. Thus, implanted defibrillators permit the patient to function in a fairly normal fashion while the defibrillator continuously monitors the activity of the heart. Implantable defibrillators are expensive, however, and are used on only a small fraction of the total population at risk for sudden cardiac death.

External defibrillators send electrical pulses to the patient's heart through electrodes applied to the patient's torso. External defibrillators are useful in the emergency room, the operating room, emergency medical vehicles or other situations where there may be an unanticipated need to provide electrotherapy to a patient on short notice. The advantage of external defibrillators is that they may be used on a patient as needed, then subsequently moved to be used with another patient. The disadvantage compared to implantable defibrillators is that the external defibrillator must be capable of effective treatment with any patient with whom it is used. Since an implantable defibrillator is used with a specific patient, the performance of the defibrillator is adjusted to provide specific electrotherapy tailored for the particular patient. Operating parameters such as electrical pulse amplitudes and total energy delivered may be effectively titrated to the physiology of the particular patient to optimize the defibrillator's effectiveness. For example, the initial voltage, first phase duration and total pulse duration may be set prior to implantation of the device to deliver the desired amount of energy or to achieve a desired start and end voltage differential (e.g., a constant tilt). Even when an implanted defibrillator has the ability to change its operating parameters to compensate for changes in the impedance of the defibrillator leads and/or the patient's heart (as discussed in the Fain patent cited below), the range of potential impedance changes for a single implantation in a patient is relatively small. Parameters such as the patient impedance can be measured at the time of implantation and the defibrillation waveform set up for the characteristics of the particular patient.

An external defibrillator, by comparison, must be designed to work with the full range of patient characteristics presented by the patients with whom the defibrillator may be used. Since external defibrillator electrodes are not in direct contact with the patient's heart, and because external defibrillators must be able to be used on a variety of patients having a variety of physiological differences, external defibrillators must operate according to pulse amplitude and duration parameters that will be effective for most patients, no matter what the patient's physiology. For example, the impedance presented by the tissue between external defibrillator electrodes and the patient's heart varies from patient to patient, thereby varying the intensity and waveform shape of the shock actually delivered to the patient's heart for a given initial pulse amplitude and duration. Pulse amplitudes and durations effective to treat low impedance patients do not necessarily deliver effective and energy efficient treatments to high impedance patients. Accordingly, the patient's thoracic impedance is usually measured by the defibrillator during the therapy and the pulse waveform adjusted dynamically as described in U.S. Pat. No. 5,803,927 (Cameron et al.) and U.S. Pat. No. 5,749,904 (Gliner et al.)

Defibrillator waveforms, i.e., time plots of the delivered current or voltage pulses, are characterized according to the shape, polarity, duration and number of pulse phases. Most modern defibrillators, internal and external, use some form of truncated exponential, biphasic waveforms. Examples of biphasic implantable defibrillators may be found in U.S. Pat. No. 4,821,723 to Baker, Jr., et al.; U.S. Pat. No. 5,083,562 to de Coriolis et al.; U.S. Pat. No. 4,800,883 to Winstrom; U.S. Pat. No. 4,850,357 to Bach, Jr.; U.S. Pat. No. 4,953,551 to Mehra et al.; and U.S. Pat. No. 5,230,336 to Fain et al.

One prior art approach to this problem of patient variability is to provide an external defibrillator with multiple energy settings that could be selected by the user. A common protocol for using such a defibrillator is to attempt defibrillation at an initial energy setting suitable for defibrillating a patient of average impedance, then raise the energy setting for subsequent defibrillation attempts in the event that the initial setting failed to resuscitate the patient. The repeated defibrillation attempts require additional energy and add to patient risk. Another approach, as indicated above, is to measure the patient impedance during therapy, or a parameter related to patient impedance, and alter the shape of a subsequent defibrillation shock based on the earlier measurement. For example, the implanted defibrillator described in the Fain patent delivers a defibrillation shock of predetermined shape to the patient's heart in response to a detected arrhythmia. The Fain device measures the system impedance during delivery of that shock and uses the measured impedance to alter the shape of a subsequently delivered shock. A variation of this technique is described in an article written by R. E. Kerber, et al., "Energy, current, and success in defibrillation and cardioversion: clinical studies using an automated impedance-based method of energy adjustment," *Circulation* vol. 77 at pp 1038-46 (May 1988). In this article the authors describe an external defibrillator that administers a test pulse to the patient prior to administering the defibrillation shock. The test pulse is used to measure patient impedance prior to shock delivery. The defibrillator then adjusts the amount of energy delivered by the shock in response to the measured patient impedance. The shape of the delivered waveform of Kerber et al. is a damped sinusoid.

While patient impedance is important and can be measured by the defibrillator at the time of therapy, another important patient characteristic is the response of the myocardial cell membrane of the patient to electrotherapy. While it is known that an electrical shock will stop the fibrillation electrical activity, the exact physiological explanation for this remains a matter of conjecture. One hypothesis is that the initial high energy shock ends the electrical activity of the myocardial cells by strong current flow in the direction of the shock polarity. The benefits of a biphasic waveform, which include better defibrillation and fewer deleterious aftereffects, are hypothesized as due to the reverse polarity of the second phase of the shock waveform. This reversal of the current during the second phase is believed to reduce residual effects of the initial shock and stabilize the tissue by removing residual charges in the myocardial cells. It is hypothesized that the myocardial cells are more susceptible to autonomous resumption of regular electrical pulsation if the effects of the initial defibrillation shock are completely removed so that they will not impede this resumption of normal electrical activity. This hypothesis leads to a desire to know the precise myocardial cell response of the patient to an electrical shock. While myocardial cell response has been measured in clinical studies, to date it has not been possible to measure this cell response during therapy. Thus, most defibrillators assume an average value of cellular response which is derived from the measured values of these studies. This use of an assumed average value leaves much to be desired. The dispersion of cellular responses about the average is poorly known in general, and a particular patient's cellular response characteristics are difficult to predict or detect. Accordingly it is desirable to design a pulse waveform for an external defibrillator which is safe and effective for patients with ranges of different patient impedances and different myocardial cell responses.

In accordance with the principles of the present invention, an external defibrillator is provided which produces a biphasic defibrillation pulse with various adjustable parameters. Among these parameters are the energy to be delivered, initial voltage and current, phase duration, pulse duration, and pulse tilt, including variable phase 2 tilt. The adjustable tilt of the second phase is provided by controllably bypassing the patient with some of the pulse current during the second phase, which adjusts the tilt of the second phase of the biphasic waveform. The present invention can be implemented by a single capacitance defibrillator.

Figure 4A:
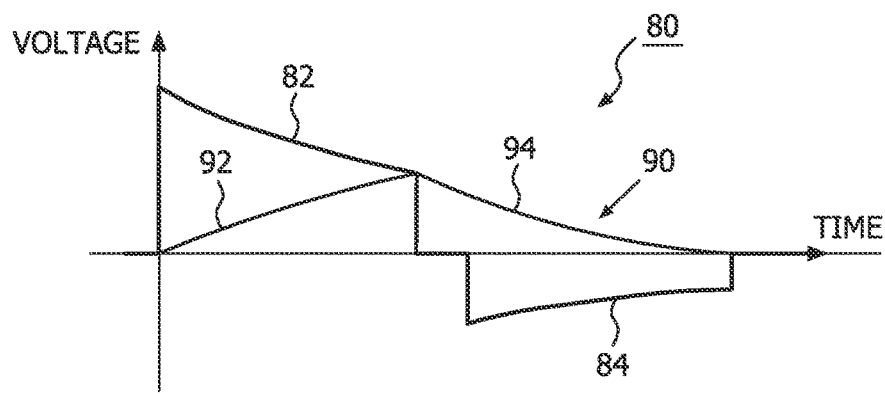
Figure 4B:
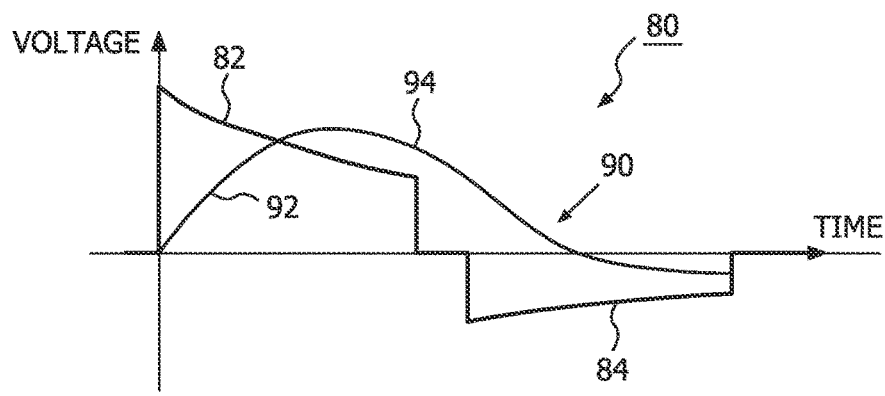
Figure 4C:
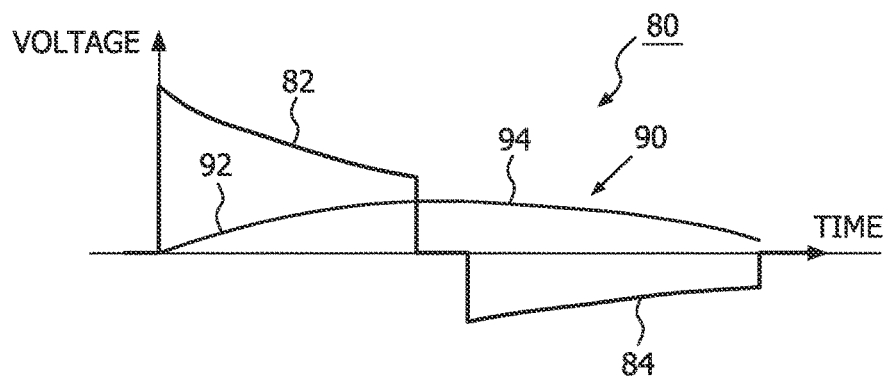

FIGS. 4a-4c each illustrates a biphasic defibrillation waveform against a different myocardial cell response characteristics.

Figure 5:
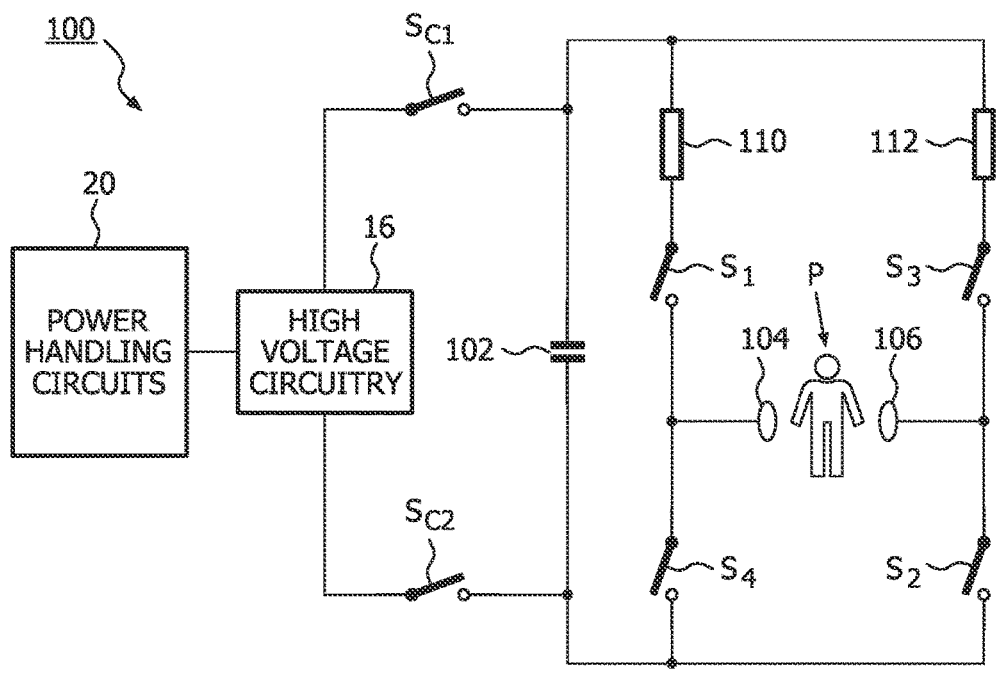

FIG. 5 schematically illustrates a defibrillator which delivers a biphasic defibrillation waveform with adjustable second phase tilt in accordance with the principles of the present invention.

Figure 6:
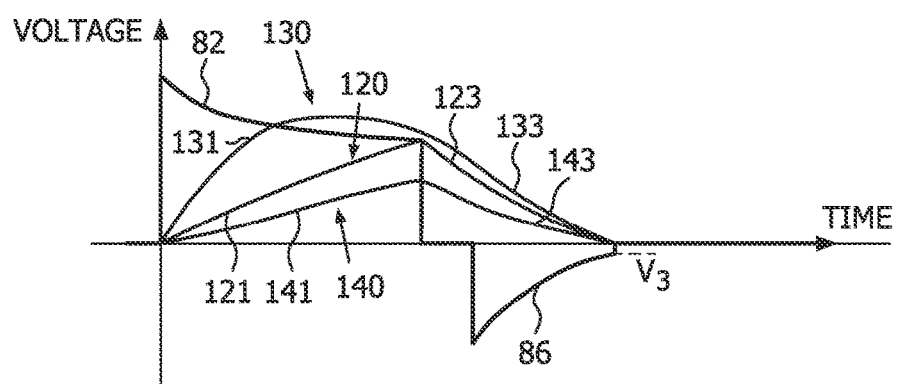

FIG. 6 illustrates a biphasic defibrillation waveform produced by the defibrillator of FIG. 5 against different myocardial cell response characteristics.

Figure 1:
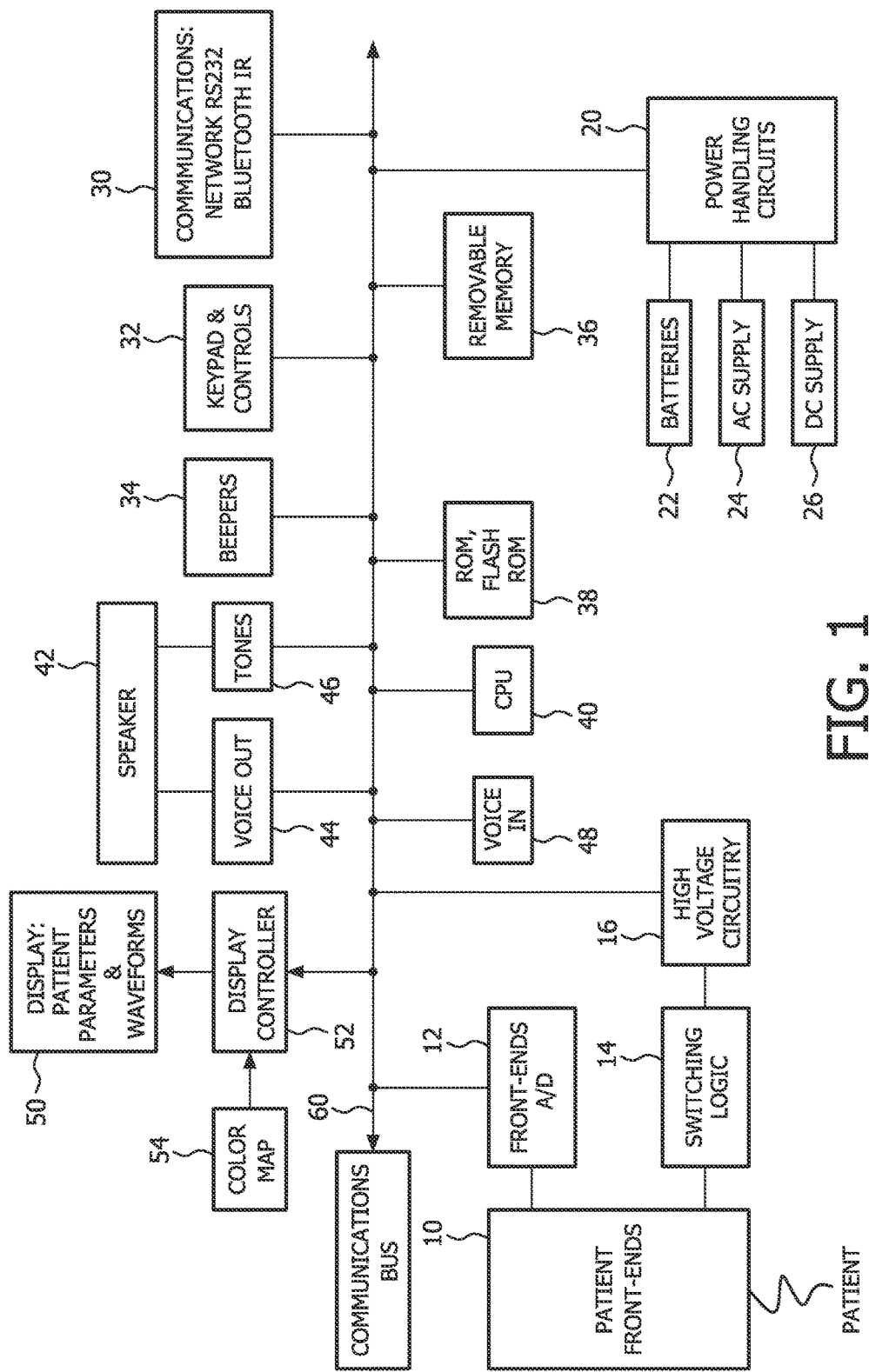
FIG. 1 illustrates in block diagram form an external defibrillator constructed in accordance with the principles of the present invention.

Referring first to FIG. 1, a patient monitor/defibrillator constructed in accordance with the principles of the present invention is shown in block diagram form. The instrument shown in FIG. 1 is capable of performing defibrillation of a patient who is experiencing ventricular fibrillation. It is also capable of performing ECG monitoring including the cardiac monitoring necessary for automatic defibrillation decision-making. The illustrated monitor is also capable of $SpO_2$ oxygen sensing, noninvasive blood pressure monitoring, and end tidal $CO_2$ monitoring. Other functions such as invasive blood pressure monitoring and patient temperature monitoring may also be found in such a multi-functional instrument. The monitor has a plurality of patient front-ends, which are input and output circuitry for the sensors and electrodes attached to the patient. This circuitry includes conventional sensing and amplification circuitry for ECG electrodes, for optical oxygen sensors, for pressure sensing and for carbon dioxide sensing, among others. The information received by the patient sensors and processed by the front-end circuitry 10 is digitized by front-end A/D converters 12. The digitized information is coupled to processing circuitry of the instrument by a communications bus 60 which connects data between the various modules of the instrument.

The instrument includes high voltage circuitry 16 for defibrillator operation. The high voltage circuitry produces the high voltage pulse necessary for defibrillation which is connected at the appropriate time by switching logic 14 to defibrillator electrodes coupled to the patient. This circuitry provides the high voltage shock needed to disrupt the ventricular fibrillation and returns the heart to a normal rhythm. The shock level and waveform delivered for defibrillation can be automatically calculated by a processor 40 in the monitor or can be manually set by an experienced medical technician or physician.

Power for the modules within the instrument is distributed by power handling circuits 20. The power handling circuits 20 will distribute power from batteries 22, from an AC supply 24, or from a DC supply 26. The AC and DC supplies are also coupled to circuitry which charges the batteries when the monitor is powered from these external power sources.

The information obtained by the instrument may be sent to other instruments or locations by communications circuitry 30. This may include a network connection, an RS232 connection, or a wireless connection (e.g. Bluetooth, WiFi or infrared, etc.).

The instrument is operated and adjusted by means of a keypad and controls 32. In a constructed embodiment the keypad is a membrane keypad providing integrity against environmental conditions. Controls such as an on/off switch, power level and shock delivery controls for defibrillation, a printer, and other functions may also be provided.

The monitor is operated under control of a central processing unit (CPU) 40. The CPU runs software stored on a read-only memory (ROM) 38. Flash ROM is also provided for the control of feature setups and new or special capabilities such as waveform information. Removable memory 36 is provided for storage of information generated during a patient episode such as ventricular fibrillation. Patient information such as cardiac waveforms before and after defibrillation are also stored on the removable memory 36, which can be removed and given to a subsequent care-giver for review, record-keeping, and subsequent diagnosis. The removable memory 36 could also record voice information from a care-giver speaking into a microphone 48.

Beepers 34 are used to drive a solid-state sound source that produces short "chirping" sounds. These sounds indicate that the instrument's resident self-test has detected a low battery level or a malfunction in a patient-critical component or circuit group. There is also a dedicated display on the front of the instrument that presents a large, flashing, red X to indicate a low battery level or a large, fixed, red X to identify a circuit failure.

Tones 46 are produced by the software and then used to drive the speaker 42. This capability is used during certain monitoring functions such as a short tone in response to each heart cycle. Combinations of tones are used to issue audible alerts and alarms when a patient's vital measurements fall outside the alarm limits selected. Tones can also be produced at a prescribed rate to guide a caregiver in the delivery of CPR compressions.

The speaker 42 can reproduce pre-recorded voice instructions and other information stored and reproduced from voice out circuitry 44.

Figure 2A:
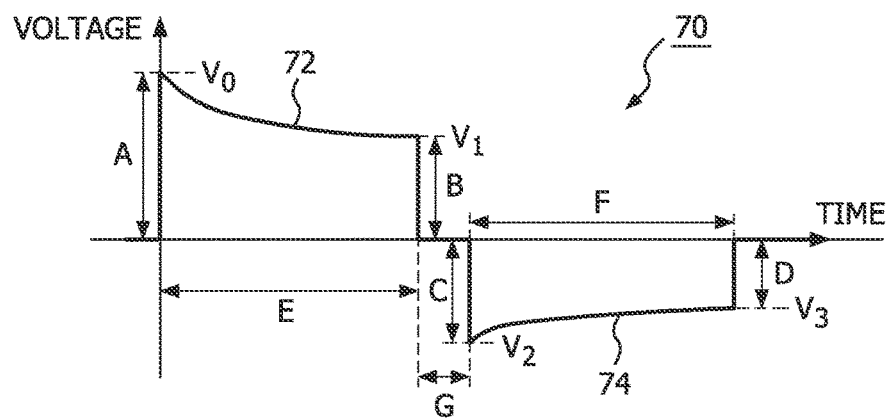
FIGS. 2a and 2b illustrate biphasic waveforms with high and low tilt characteristics.

FIG. 2a illustrates a biphasic waveform 70 of the type which is produced by a defibrillator constructed in accordance with the present invention. The biphasic waveform has a first phase 72 of one polarity and a second phase 74 of an opposite polarity. Biphasic waveforms may be delivered by a defibrillator with one or two capacitors. In the case of a two-capacitor defibrillator, one capacitor will be charged to the maximum voltage $V_0$ at the start of the first phase 72 and the other capacitor will be charged to the maximum voltage $V_2$ at the start of the second phase. The two capacitors will be oriented in different polarities with respect to the high voltage delivery circuit so that opposite phase pulses will be produced. During the first phase the first capacitor is coupled to the high voltage delivery circuit and discharges its current through the defibrillator electrodes. When it is desired to end the first phase the first capacitor is switched out of the delivery circuit and the second capacitor is switched in. Since the second capacitor is switched in with a reverse polarity to that of the first capacitor, the discharge of the second capacitor will produce a pulse polarity for the second phase which is the inverse of that of the first phase. When two capacitors are used, each one can be charged to a desired voltage level, independent of the other.

In practical devices two-capacitor arrangements are rarely implemented. Such arrangements have drawbacks of large size and cost. Thus, external defibrillators generally employ a single capacitor for reduced cost and size. When using a single capacitor to deliver a biphasic waveform, an H bridge is used to switch the waveform. During the first phase of the waveform, the H bridge connects the two terminals of the capacitor to the electrodes. At the end of the first phase that connection is opened and the terminals of the capacitor are switched to connect in the reverse polarity to the electrodes. Since high currents are often being switched at this time, there is often a pause between phases as shown by time interval G in FIG. 2a. Because only one capacitor is being used, the voltage on the capacitor at the end of the first phase is the starting voltage at the beginning of the second phase, when the connection of the capacitor is switched. In FIG. 2a, this would mean that $V_2=-V_1$.

FIG. 2a illustrates other waveform parameters that are important for efficacy. One is the relative phase duration, the relation of the duration E of the first phase to the duration F of the second phase. A target duration relationship that is often used is 60% to 40%. That is, it is desirable that, of the total waveform duration, the first phase occurs for 60% of the time and the second phase occurs for 40% of the time. Total waveform duration (E+G+F) is also important. It is desirable that the waveform duration be long enough to defibrillate the patient, but also be short so as not to cause electrical injury to the patient. Stated another way, it is desirable to only shock the patient for the time needed to cause defibrillation; extended energy delivery which does not improve the effectiveness of defibrillation should be avoided. Biphasic waveforms are generally employed with total durations in the range of 5 msec to 20 msec.

Another waveform parameter that is significant is what is known as waveform "tilt." The tilt is an indicator of the energy delivery and is expressed as a percentage of the starting and ending voltages of the waveform. The equation for calculating the waveform tilt is:

$$\text{Tilt}=1-(V_3/V_0)\%$$

where $V_0$ is the initial voltage of the waveform (waveform amplitude A) and $V_3$ is the ending voltage (waveform amplitude D) in FIG. 2a. Tilt can also be calculated for each phase of the waveform individually.

FIG. 2a illustrates what is known as a low tilt waveform. Low tilt waveforms are commonly encountered when delivering the pulse waveform to a patient with a high thoracic impedance. With voltage, current and patient impedance related by Ohm's Law, a high patient impedance for a given starting pulse voltage $V_0$ would result in a relatively low current flow, and the voltage decline over the pulse duration would be relatively low. FIG. 2a illustrates a relatively small voltage decline over the first phase 72 of the waveform 70 from $V_0$ to $V_1$, and over the second phase 74 from $V_2$ to $V_3$.

Figure 2B:
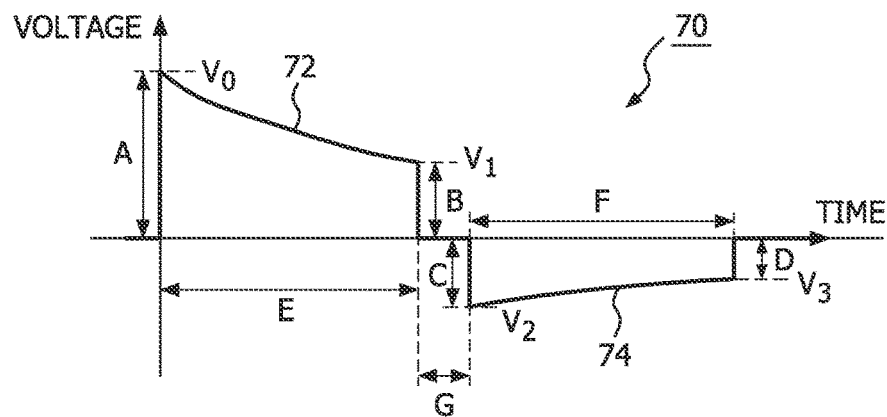

FIG. 2b illustrates a high tilt waveform, commonly encountered with a low impedance patient. With the low patient impedance, the current flow is higher for a given voltage and the voltage decline during waveform delivery is greater than that of the low tilt waveform of FIG. 2a. From the same starting voltage $V_0$, the first phase 72 of the waveform declines to a lower $V_1$ (waveform amplitude B) than was the case for the low tilt waveform of FIG. 2a. Similarly, there is a greater decline from $V_2$ (waveform amplitude C) to the ending voltage $V_3$ during the second phase 74.

Figure 3:
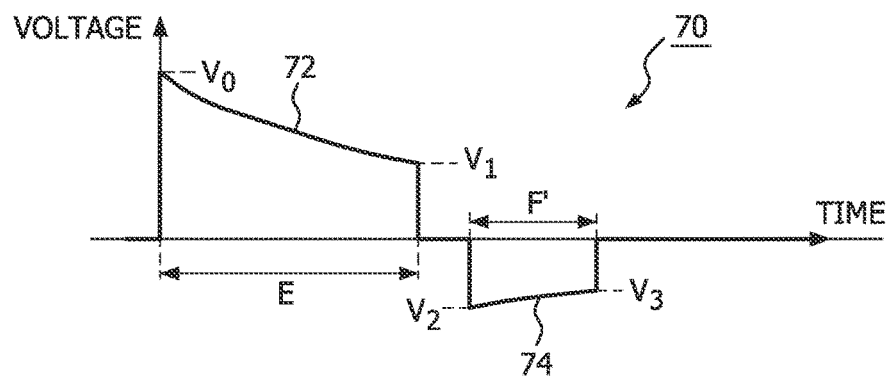
FIG. 3 illustrates a truncated biphasic waveform.

A corollary to the tilt characteristic is that a high tilt waveform will decline to a given ending voltage in less time than will a low tilt waveform for the same ending voltage. This means that the low tilt waveform can last for an appreciable, perhaps excessive, amount of time to reach the same ending voltage. Since defibrillation is generally believed to occur during the initial few milliseconds of the first phase when the current delivery is strongest, perhaps just the initial 7 milliseconds when the average current is highest, this means that much of the time of the extended low tilt waveform may be of little therapeutic efficacy and hence unnecessary. One prior art solution to this situation is to truncate the second phase 74 of the waveform 70 as illustrated in FIG. 3. The first phase 72 will start at its initial voltage level $V_0$ and extend for some preprogrammed or impedance-tailored duration E or until a determined voltage $V_1$ is reached. The second phase 74 begins at its initial voltage $V_2$ as before, but is prematurely terminated or truncated after a time F'. The second phase duration F' can be set for the second phase alone or in consideration of maintaining a maximum overall waveform duration (E+F'). For instance, the second phase 74 of the waveform can be truncated when F' is equal to E, and the relative phase durations are 50:50.

A problem with second phase truncation is that it ends the delivered pulse with an appreciable voltage still applied to the myocardium at the termination of the waveform. In FIG. 3, the final $V_3$ voltage is greater than the ending voltage would be if the second phase were allowed to decline further. This appreciable termination voltage can have adverse effects on the effectiveness of the therapy. It is ideally desirable that the terminal voltage of a defibrillation waveform be zero, so that there is no residual charge left on the myocardial cells after pulse delivery which could deleteriously affect the body's autonomous restarting of the heart's electrical pulsation. This removal of residual charge has been referred to by one commentator as "burping." See U.S. Pat. No. 5,991,658 (Brewer et al.) Another benefit of terminating the defibrillation waveform with as small a voltage as possible is that sensitivity of calculation of the optimal dose of the second phase to uncertainties in cellular response characteristics peculiar to a particular patient application are thereby minimized. A third benefit of terminating the defibrillation waveform at near zero voltage is avoidance of the phenomenon of "break excitation"—the stimulation of post-shock arrhythmia via current induced by a large change in voltage. One way to achieve this goal is to allow the phases of a biphasic pulse to completely decay to zero volts, as shown in U.S. Pat. No. 6,539,255 (Brewer et al.) The desirability of doing so can be appreciated from FIGS. 4a-4c, which illustrate biphasic waveforms 80 over which are drawn myocardial cell response characteristics 90. As previously mentioned, the myocardial cell response can vary from patient to patient and even from day to day, and is generally not known for a given patient at the time of a rescue. FIG. 4a illustrates how the myocardial cell response will vary in an ideal situation. The variation of the myocardial cell response characteristic can be characterized by a cell membrane time constant Ʈ which nominally is 3.5 milliseconds. In the case of FIG. 4a this time constant causes the myocardial cell response characteristic 90 to rise during the first phase 82 of the biphasic waveform 80 until it peaks at the end of the first phase. When the pulse waveform switches to the second phase 84, the myocardial cell response characteristic declines as shown by the latter portion 94 of the response characteristic. In this case the response characteristic has declined to exactly its initial starting level at the end of the second phase 84. This indicates that there is no residual charge on the cell membranes of the myocardium at the end of the pulse 80.

FIG. 4b illustrates a situation in which the myocardial cell response characteristic 90 has a lesser time constant Ʈ which causes the response characteristic to reach its peak before the end of the first phase 82 of the biphasic pulse 80. Thereafter the response characteristic declines with the decline of the waveform tilt, a response which is believed to contribute very little to defibrillation. During the second phase 84 of the biphasic pulse the response characteristic continues its more rapid change, declining below its starting level and following the decline of the tilt of the second phase until the second phase 84 of the pulse terminates. It is seen that, at its termination, the response characteristic is below its starting level, indicating that some residual charge remains on the myocardial cell membranes. This situation is a case which may occur with a low impedance patient.

FIG. 4c illustrates a high impedance patient situation, where the myocardial cell response characteristic 90 rises very slowly as shown at 92 during the first phase 82 of the biphasic waveform 80. The response characteristic is still rising at the time the first phase 82 ends. When the second phase 84 of the pulse is applied, the response characteristic begins a gradual decline, not quite reaching its initial starting level at the end of the second phase. Again, this is indicative of residual charge on the cell membranes of the myocardium.

In accordance with the principles of the present invention, a defibrillator circuit 100 which addresses these conditions is shown in FIG. 5. In this circuit the energy for biphasic pulse delivery is stored on a single capacitor 102. In preparation for pulse delivery a battery or power supply of the power handling circuits 20 is coupled to high voltage circuitry 16. Switches $S_{c1}$ and $S_{c2}$ close and the high voltage circuitry 16 charges the capacitor 102 to a high voltage level $V_0$ such as 2000 volts. When the capacitor 102 is fully charged to the desired level the switches $S_{c1}$ and $S_{c2}$ open. An H-bridge circuit comprising switches $S_1$, $S_2$, $S_3$ and $S_4$ is then switched to deliver a biphasic pulse to a patient P through electrodes 104 and 106. During the first phase of the biphasic pulse switches $S_1$ and $S_2$ are closed and the capacitor is coupled to the patient electrodes with current flowing through the patient in one direction, for example, from chest electrode 104 to chest electrode 106. A small resistor 110, for instance 10Ω, limits peak current to prevent injury to a low impedance patient. At the end of the first phase switches $S_1$ and $S_2$ open to end the first phase of the biphasic pulse and switches $S_3$ and $S_4$ close to deliver the second phase of the pulse to the patient P. The closure of these switches causes current from the capacitor 102 to flow in the reverse direction as that of the first phase, from chest electrode 106 to chest electrode 104 in this example. A small resistor 112, also of 10Ω, for example, may also be used in series with the second phase current path. In accordance with the principles of the present invention, switch $S_1$ is also closed for some duration of the second phase pulse. In a preferred embodiment switch $S_1$ is switched between closed and open during the second phase by pulse width modulation control of the switch. The closure of switch $S_1$ causes some of the current of the capacitor 102 to bypass the patient P through the path formed by switches $S_1$ and $S_4$ when switch $S_1$ is closed during the second phase. As a result, the voltage of the capacitor 102 drops more rapidly than it would if switch $S_1$ were not used during the second phase. The resultant effect on the biphasic waveform is shown in FIG. 6, which is seen to be a rapid decline (higher tilt) of the second phase 86 of the biphasic pulse. By control of the closure of switch $S_1$, the second phase 86 of the biphasic pulse can be brought to near reference potential at the termination of the biphasic waveform, and in a shorter time than would occur if switch $S_1$ were not used during the second phase. The ending voltage $V_3$ at the end of the biphasic pulse is brought to near zero by this operation.

The measurement of the patient impedance, which can be done with a small signal transmission prior to shock delivery as described in the Kerber et al. paper or by measuring the delivered current or voltage during actual delivery of the high voltage pulse, as illustrated in the aforementioned US patents to Fain et al., to Cameron et al., and to Gliner et al., can be used to control parameters of the delivered shock waveform such as energy, capacitor charge voltage, and waveform durations as shown in these patents and in U.S. Pat. No. 5,352,239 (Pless).

The effect of this controllable decline or tilt of the second phase of the biphasic pulse is that the pulse waveform can be made to terminate near its reference potential. This is illustrated by the three myocardial cell response characteristics drawn over the biphasic pulse waveform in FIG. 6. In the case where the biphasic pulse happens to closely match the cell response, as shown by myocardial cell response characteristic 120, the response characteristic rises to near the terminating corner of the first phase 82 of the biphasic pulse, then declines during the second phase 86 as shown by portion 123 of the response characteristic until the characteristic ends near the final voltage level $V_3$. For a low impedance patient, as indicated by response characteristic 130, the response characteristic again rises rapidly during the first phase 82 as shown by curve 131, and also declines during the second phase 86 of the biphasic pulse to end near the final voltage level $V_3$. For a high impedance patient, the initial portion 141 of the response characteristic 140 rises during the first phase 82, then declines to near the final voltage level $V_3$. The disparity between the end points of all of the myocardial cell response characteristics of FIG. 6 is seen to be very small, unlike those of FIGS. 4a-4c, indicating that in all cases little residual charge remains on the cell membranes. The waveform voltage ends up near zero, regardless of the patient impedance. This is accomplished in spite of the lack of any a priori myocardial cell response characteristic information by the defibrillator.

In a preferred embodiment, as previously mentioned, the tilt of the second phase of the biphasic pulse is controllably increased or adjusted by switching switch $S_1$ between open and closed conditions during the delivery of the second phase of the biphasic pulse. This pulse width modulation control can be performed while monitoring the voltage of the capacitor 102. Other switch control techniques may be employed such as closing switch $S_1$ for a single interval of a predetermined duration. In the preferred embodiment a 200 microfarad capacitor is used for capacitor 102. The present invention may be implemented with a single capacitor defibrillator or with a multiple capacitor defibrillator in which different capacitors or capacitor combinations are used during the two phases of the delivered waveform. In the preferred embodiment the second phase tilt is controlled to maintain an overall waveform tilt of about 95%. Increasing the tilt during the second phase also has the beneficial effect of enabling effective treatment with a reduced range of waveform durations, with the preferred embodiment producing biphasic pulse waveforms ranging from 6.5 milliseconds to 12 milliseconds over the full patient impedance population, a marked reduction from the conventional pulse duration maximum of 20 milliseconds.

What is claimed is:

1. An external defibrillator which delivers biphasic defibrillation pulses comprising:
a high voltage circuit;
a capacitor, coupled to the high voltage circuit which is charged by the high voltage circuit for defibrillation pulse delivery;
a pair of patient electrodes;
a plurality of switches, coupled between the capacitor and the patient electrodes, and operable to couple first and second phases of a biphasic defibrillation pulse waveform to the patient electrodes, wherein the tilt of the second phase of the waveform is controllably adjustable; and
a controllable current path which enables current to controllably bypass the patient electrodes during the second phase of the biphasic waveform, the high voltage circuit operable to close at least one of the plurality of switches to enable the bypass current during the second phase of the biphasic waveform.

2. The external defibrillator of claim 1, wherein the plurality of switches comprises an H-bridge with one switch closure configuration for delivery of one phase of a biphasic waveform and another switch closure configuration for delivery of an opposite phase of the biphasic waveform.

3. The external defibrillator of claim 1, wherein the capacitor comprises a single capacitance which is used for delivery of both phases the of biphasic waveform.

4. The external defibrillator of claim 1, wherein the capacitor further comprises a first capacitor which is used for delivery of the first phase of a biphasic waveform and a second capacitor which is used for delivery of the second phase of the biphasic waveform.

5. The external defibrillator of claim 1, wherein the plurality of switches comprises an H-bridge, and wherein the controllable current path includes a switch of the H-bridge.

6. The external defibrillator of claim 5, wherein the H-bridge further comprises first and second switches which are closed for pulse delivery during the first phase of the biphasic waveform, and third and fourth switches which are closed for pulse delivery during the second phase of the biphasic waveform, wherein the controllable current path includes one of the first and second switches.

7. The external defibrillator of claim 6, further comprising a first resistor coupled in series with the first and second switches when the first and second switches are closed, and a second resistor coupled in series with the third and fourth switches when the third and fourth switches are closed.

8. The external defibrillator of claim 1, wherein the controllable current path is controlled by a pulse width modulated control signal during the second phase of the biphasic waveform.

9. The external defibrillator of claim 1, wherein the biphasic defibrillation pulse waveform exhibits:
a first phase during which the pulse voltage increases from a reference potential to a voltage peak V0 and declines from V0 during the first phase of the waveform; and
a second phase which begins at an initial voltage V2 and declines from V2 during the second phase of the waveform to a level at or near the reference potential.

10. The external defibrillator of claim 9, wherein voltages V0 and V2 are of opposite sense relative to the reference potential.

11. The external defibrillator of claim 1, further comprising a circuit adapted to measure patient impedance, wherein parameters of the biphasic defibrillation pulse waveform are set in accordance with the measure of patient impedance.

12. The external defibrillator of claim 1, wherein the overall tilt of the biphasic waveform is maintained at approximately 95% through control of the tilt of the second phase of the waveform.

13. The external defibrillator of claim 12, wherein the overall tilt of the biphasic waveform is maintained at approximately 95% through an increase of the tilt of the second phase of the waveform.

* * * * *